(12) United States Patent
Pokorny et al.

(10) Patent No.: US 8,387,835 B2
(45) Date of Patent: Mar. 5, 2013

(54) APPLICATION DEVICE

(75) Inventors: Walter Pokorny, Gais (AT); Wolfgang Wachter, Schaan (LI); Klaus Galehr, Schlins (AT); Gottfried Rohner, Altstätten (CH); Ralf Suffel, Haag (CH)

(73) Assignee: Ivoclar Vivadent AG, Schaan (LI)

( * ) Notice: Subject to any disclaimer, the term of this patent is extended or adjusted under 35 U.S.C. 154(b) by 484 days.

(21) Appl. No.: 12/655,643

(22) Filed: Jan. 5, 2010

(65) Prior Publication Data

US 2010/0181344 A1 Jul. 22, 2010

(30) Foreign Application Priority Data

Jan. 22, 2009 (DE) .................. 10 2009 005 697

(51) Int. Cl.
*B67D 7/18* (2010.01)
*B67D 7/42* (2010.01)

(52) U.S. Cl. .................... 222/326; 222/567; 222/478

(58) Field of Classification Search ............ 222/326, 222/162, 163, 567, 568, 386, 405, 319, 320, 222/207; 433/90

See application file for complete search history.

(56) References Cited

U.S. PATENT DOCUMENTS

| 3,729,031 | A | * | 4/1973 | Baldwin | 141/2 |
| 4,492,576 | A | * | 1/1985 | Dragan | 433/90 |
| 5,059,121 | A | * | 10/1991 | Schulz et al. | 433/88 |
| 5,441,180 | A | * | 8/1995 | Woodruff | 222/327 |
| 5,626,265 | A | * | 5/1997 | Woodruff | 222/327 |
| 6,120,174 | A | * | 9/2000 | Hoag et al. | 366/139 |
| 6,425,885 | B1 | * | 7/2002 | Fischer et al. | 604/218 |
| 7,448,557 | B2 | * | 11/2008 | Ray et al. | 239/346 |
| 7,624,993 | B2 | * | 12/2009 | Kikuchi et al. | 277/641 |

FOREIGN PATENT DOCUMENTS

| DE | 1398907 U | 2/1937 |
| DE | 4232062 A1 | 4/1993 |
| EP | 1020167 A2 | 1/2010 |

* cited by examiner

*Primary Examiner* — Kevin P Shaver
*Assistant Examiner* — Charles P Cheyney
(74) *Attorney, Agent, or Firm* — Ann M. Knab; Thad McMurray

(57) ABSTRACT

The invention relates to an application device for dental materials with a cartridge that has a piston and is destined for receiving the dental material, and with an application nozzle that is attached to an outlet port of the cartridge. A positive or form-fit connection between the cartridge (12) and the application nozzle (14) is formed, and the application nozzle (14) and/or the cartridge (12) have a vent duct (40) whose width or diameter prevents or blocks the dental material from flowing out.

13 Claims, 3 Drawing Sheets

APPLICATION DEVICE

CROSS-REFERENCE TO RELATED APPLICATIONS

This application claims foreign priority benefits under 35 U.S.C. §119(a)-(d) from German patent application ser. no. P 10 2009 005 697.1 filed Jan. 22, 2009.

TECHNICAL FIELD

The invention relates to an application device for dental material including a cartridge having a piston and being adapted to receive the dental material.

BACKGROUND OF THE INVENTION

An application device of this kind has been known for a long time. Reference is made for example to DE 1 398 907 A1. This solution indeed, does not relate to dental materials but a hand lotion, however, comprises a cartridge and an application nozzle. Between the two components a positive locking is provided, and openings are formed for the ventilation and exhaust of the cartridge. The openings can be provided either at the cartridge or at the application nozzle.

One disadvantage of a solution of this kind is the fact that also material that is to be pressed, can exit or escape there. This may be relatively uncritical in the case of a hand lotion, since the material exiting there after the exhaust has been realized by exerting pressure on the piston of the cartridge, can be removed in a relatively uncomplicated manner.

On the other hand, however, dental materials are often of high quality such that losses are to be avoided. In the raw condition, dental materials frequently also comprise reactive substances. Free radicals in monomers of light-curable dental materials are to be taken into account, but also chemical compounds used in pastes that only achieve a stable and non-reactive condition by burning them in a dental burning oven.

In this respect, in order not to realize a contamination especially in the region of the application nozzle, it has also become known to realize the exhaust in the piston region. Especially with expendable or single-use nozzles this is uncritical, since if dental material escapes at this location, it remains relatively protected in the cartridge region between the plunger of the piston and the piston handle. Such a solution is obvious for example from DE 200 10 417 that also provides for a specific valve.

This solution, however, is complicated and can basically only be employed reasonably if the cartridge is kept suspended such that the amount of air remaining in the dental material appears adjacent to the piston plunger.

With dental materials, on the other hand, the problem arises that also in the region of the application nozzle the inclusion of air pockets or bubbles should be avoided if possible. Such air pockets or bubbles lead to a significant deterioration of the restoration result, since in the case of air inclusions the dental material is typically weakened such that cavities develop that are prone to contamination. If necessary, the aesthetic appearance of the restoration part needs further treatment or finishing, too.

Accordingly, in order to possibly avoid air inclusions of this kind, it has been proposed to keep the cartridges suspended and when connecting the application nozzle to pay attention to the fact that no air inclusions possibly remain. Typically, a collar of the application nozzle extends into the cartridge. Especially in a collar arrangement of this kind there is the danger of air accumulating behind the collar, more precisely at the highest position of the cartridge or, as the case may be, air being entrained if the piston is actuated.

Even in the case that a collar of this kind is not provided, however, there is the possibility that air inclusions remain which are then entrained. In this connection it has already been proposed to impart a truncated conical construction to the upper end wall or front wall of the cartridge. In the case of a rather viscous dental material, however, the possibility exists that the dental material or mass already extends at least partially into the nozzle grommet or spout of the application nozzle and thus closes off against the edge at the transition region between the conical part and the grommet or spout. This may result in air inclusions, too, in which case the danger arises that the air inclusions are entrained.

OBJECTS AND SUMMARY OF THE INVENTION

Therefore, the invention is based on the object of providing an application device for dental masses which is better suitable for providing an undisturbed operation of the device, especially in the case of an optimized storage of the cartridges.

According to the invention it is especially expedient if an inventive and exactly defined vent duct is formed between the application nozzle and the cartridge, more precisely at the transition region therebetween and thus adjacent to the outlet port of the cartridge, or adjacent to the transition region. Advantageously, said vent duct is slot-shaped in cross-section and thus is smaller in height than in width. It is to be understood that a lengthwise oval embodiment or design is also possible without departing from the scope of the invention. By means of the comparatively small height it is achieved that the dental material due to its cohesiveness is not capable of entering the slot. Air that accumulates at this location, however, can escape without problems which is desired according to the invention.

For example, the width/height-ratio can amount to more than 2:1, but preferably more than 4:1 or also 10:1. Alternatively, it is also possible to realize a plurality of small and circular vent duct inlet ports that practically serve as a kind of filter and that also block or close off the inflow of dental material.

According to the invention, it is also especially expedient in this connection to provide the vent duct with a plurality of blocking stages. Even if the pressure in the dental material then overcomes the cohesiveness of the dental material for the first blocking stage, in the next blocking stage and also in the further blocking stages additional friction is produced, whereas the friction then preferably is of such dimension that if the cartridge is entirely squeezed empty, still no material escapes from the vent duct to the outside.

It is particularly advantageous, if the design and/or the diameters at the transition region between the application nozzle and the cartridge are formed in a suitable manner such that the vent duct is formed at this location. This enables the creation of the inventive application nozzle without additional tool modifications, more precisely like a slide for the realization of a hole in the front wall of the cartridge.

A particularly preferred embodiment provides that the vent duct is realized at the entire periphery. The exact rotary position of the cartridge is then not relevant for the function of the vent duct; this also applies if the cartridge is arranged transversely in practice such that the application nozzle is located transversely above the cartridge.

In this connection it is especially expedient if the filling of the cartridge takes place at this position so that the dental material is introduced into the cartridge bottom-up, and entrapped air, should the situation arise, can accumulate in the region of the outlet port of the cartridge.

In a modified embodiment, however, it is also possible to attach the vent duct—or, if applicable, several air ducts distributed about the periphery—in such a manner that a seal or gasket between the application nozzle and the cartridge is interrupted at the position at which the vent duct is to be located. The seal or gasket can also be incorporated integrally into the application nozzle or into the cartridge.

According to the invention it is particularly favourable if the seal or gasket nearly completely forms a seal between the cartridge and the application nozzle in a circular manner.

According to the invention it is particularly favorable if the vent duct at least at one location, for example at its inlet, seals off elastically. By means of the air pressurized by the pressure arising upon the actuation of the piston, the vent duct then opens against the elasticity of its defining walls; as soon as the air has escaped and the pressure thus has decreased, the vent duct is closed again.

According to the invention it is especially expedient that a positive connection or locking is formed between the cartridge and the application nozzle.

According to the invention it is particularly expedient that the application nozzle covers an outlet port of the cartridge and is connected to the cartridge in particular in a releasable manner.

According to the invention it is particularly expedient that the air duct is formed at the transition region between the application nozzle and the cartridge.

According to the invention it is particularly expedient that the cartridge at the perimeter region of its outlet port in particular has a truncated conical tapering shape and that a connecting region of the application nozzle comprises a corresponding counter contour, and that the taper in particular at least partially is covered by the connecting region of the application nozzle.

According to the invention it is particularly expedient that the vent duct extends along a seal or gasket between the application nozzle and the cartridge, in particular between the ends of the seal or gasket, said seal or gasket at least partially extending along a perimeter region of the outlet port.

According to the invention it is particularly expedient that at least part of the vent duct comprises at least one deflection at the seal or gasket, thus elongating the vent duct, said vent duct in particular having the shape of a labyrinth.

According to the invention it is particularly expedient that the dental material collects or accumulates at the inlet of the vent duct and seals the vent duct.

According to the invention it is particularly expedient that the vent duct at least comprises a slot or narrow gap whose height is dimensioned so small that upon actuation of the piston dental material cannot penetrate or get through.

According to the invention it is particularly expedient that the gap is smaller than 1 mm, in particular smaller than 0.5 mm, and that a filter that is permeable to air, in particular is arranged in the vent duct.

According to the invention it is particularly expedient that several slots are arranged one after another in the vent duct in flow direction, said slots being formed by a side wall of the application nozzle or the cartridge defining the vent duct, said side wall being serrated in cross-section.

According to the invention it is particularly expedient that the dental material is a plastic material that can be cured by light and/or heat, and that the dental material is especially used for the production of implants, in particular dentures.

According to the invention it is particularly expedient that several, in particular elastic lips are arranged one after another in the direction of flow within the vent duct.

According to the invention it is particularly expedient that the cartridge has a circle-symmetric shape in the region of its outlet port and/or its taper.

According to the invention it is particularly expedient that the vent duct is arranged along the entire periphery in particular in the transition region between the taper and the application nozzle and forms a barrier for the dental material.

According to the invention it is particularly expedient that the application nozzle in its operational position is arranged above, in particular transversely above the cartridge.

According to the invention it is particularly expedient that an application device is used in an injection apparatus that comprises an extrusion device working or acting together with the piston of the application device.

BRIEF DESCRIPTION OF THE FIGURES

Further details, advantages and features of the invention emerge from the following description of several embodiments of the invention in connection with the drawings, in which.

DETAILED DESCRIPTION

Figure 1:
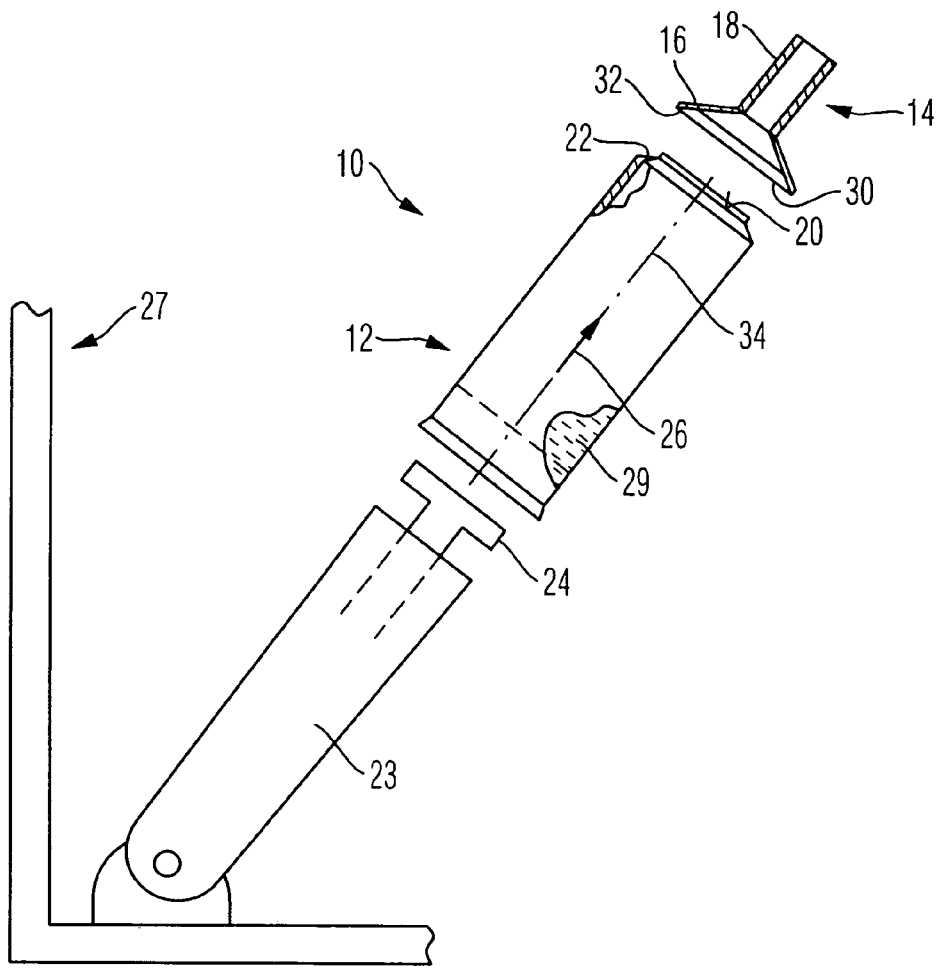
FIG. 1 is a schematic side view of a first embodiment of an application device according to the invention.

The application device 10 shown in FIG. 1 comprises a cartridge 12 and an application nozzle 14. The application nozzle 14 is connected to the cartridge 12 in any suitable force- or form-locked manner. Preferably, the connection is effected with the aid of a locking or latching bead which is formed and which latches upon application of force in order to slide or press open the application nozzle 14 so that the form-locking connection can be realized, or with the aid of a thread engagement or any other suitable connection, for example by means of a bayonet lock or anything similar.

The application nozzle 14 in this connection comprises a substantially truncated cone shaped connecting region 16 as well as an outlet grommet 18, which are formed in one piece or integrally.

The cartridge 12 at its outlet port 20 is embodied in a slightly conical manner. A conical edge 22 at the periphery of the outlet port 20 is formed that mates with the connecting region 16.

As can be seen in detail from the further drawing figures, the conical edge 22 is formed in a suitable manner for connecting to the connecting region 16, so that a secure connection may be established that is further pressure-resistant.

Moreover, the connection range 16 of the application nozzle is formed in such a manner that it overlaps and covers the conical edge 22, whereas the covering preferably reaches to the outer edge of the cartridge, and the cartridge—having the application nozzle 14 fitted thereto—can easily be handled without the application nozzle 14 inadvertently coming loose.

According to the invention it is particularly expedient if the operating position of the application nozzle, more precisely preferably both during the filling process and the application process, is selected so that the outlet port 20 incidentally is situated above the cartridge 12. In this way, the cartridge has an upright or substantially upright position.

A plunger 24 for applying the dental material is provided that is introduced into the cartridge 12 at the end opposing the outlet port. This plunger 24 is not yet used for the filling. FIG. 1 shows diagrammatically that the cartridge 12 is filled in the direction of the arrow 26, more precisely bottom-transversely up. The entering dental mass that absolutely still can include air inclusions, is filled in till the outlet port 20. Entrained air inclusions then collect at the uppermost position of the cartridge 12 at the position according to FIG. 1, more precisely at the conical edge 22, provided that the viscosity of the filled-in dental mass is sufficiently low, as it is provided according to the invention.

Below the conical edge 22 or adjacent thereto, typically several small air bubbles or one air bubble collect, since this position represents the highest point of the cartridge, whereas with a freshly filled cartridge which is then already provided with the respective application nozzle 14, the entire air typically only collects there in the course of time.

According to the invention it is expedient if the cartridge 12 is maintained and also employed in an upright or transversely upright position according to FIG. 1, but in particular, that a vent duct is formed between the application nozzle 14 and the cartridge 12. In this connection, an extrusion device 23 is provided that comprises an plunger 24 that can be introduced into the cartridge 12. The extrusion device 23 is supported on a frame 27 of an injection apparatus. During operation, the plunger 24 seals off against the inner wall of the cartridge 12, so that the plunger is capable of completely pressing or squeezing out the dental mass 29 received therein from the cartridge 12, more precisely through the outlet port 20.

Since the application nozzle 14 with its mounting flange or clamping collar 30 extends into the cartridge 12 at the outlet port 20, it is preferred to select the diameter of the cartridge at least at one location of the periphery or, if applicable, distributed along the entire periphery, to be so large, that a vent duct forms. The air, drained off or dissipated in this manner, then may escape into the transverse gap between the covering collar 32 of the application nozzle 14 and the outside of the conical edge 22.

It is to be understood that the design of the covering collar 32 to a large extent can be adapted to the requirements and in particular to the precise design of the outlet port 20. In particular, it is also possible to still further pull down the covering collar 32 so that it at least partially extends parallel to the axis 34 of the cartridge.

In a modified embodiment it is provided that instead of the inclined surface, more precisely the conical edge 22 of the cartridge 12, a nearly entirely cylindrical shape is provided. With this solution, a thread, a bayonet lock or some else positive or form-fit connection between the application nozzle 14 and the cartridge 12 next to the outer periphery of the cartridge 12 is provided, and in the extreme case, the vent duct 40 which is best shown in the right-hand representation in FIG. 2, can be formed by a simple slot.

It shall also be understood that the embodiment or design of the application nozzle with or without grommet or spout or, for example with a hose connection, can be adapted to the requirements to a large extent. In any case it is essential that air possibly collected at the highest position of the cartridge 12, can be entirely discharged via the vent duct 40 and cannot get into the application nozzle 14.

Figure 2:
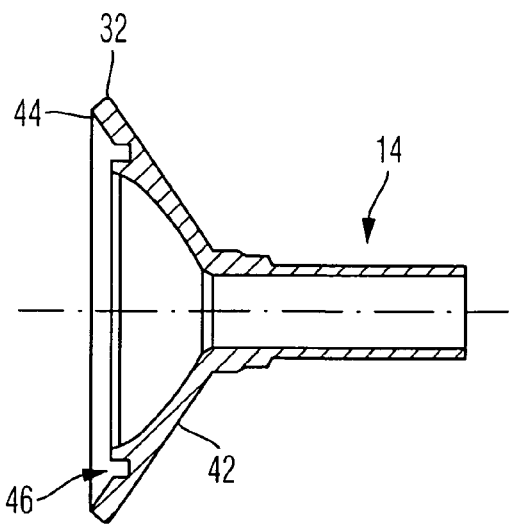
FIG. 2 is an enlarged detail of the application nozzle as shown in FIG. 1.

FIG. 2 shows how the application nozzle 14 and the vent duct 40 can be embodied.

As can be seen from FIGS. 1 and 2, the outlet grommet or spout 18 comprises the mounting flange 30 that partially extends into the cartridge 12, and the covering collar 32. The covering collar 32 extends into the extension of the conical body 42 of the application nozzle 14 in substantially the same inclined or angular angle as the conical edge 22 of the cartridge.

Figure 2A:
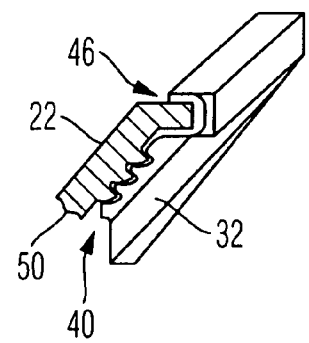
FIG. 2a is a further enlarged detail of the application nozzle as shown in FIG. 1, showing it secured to the end portion of the cartridge.
Figure 3:
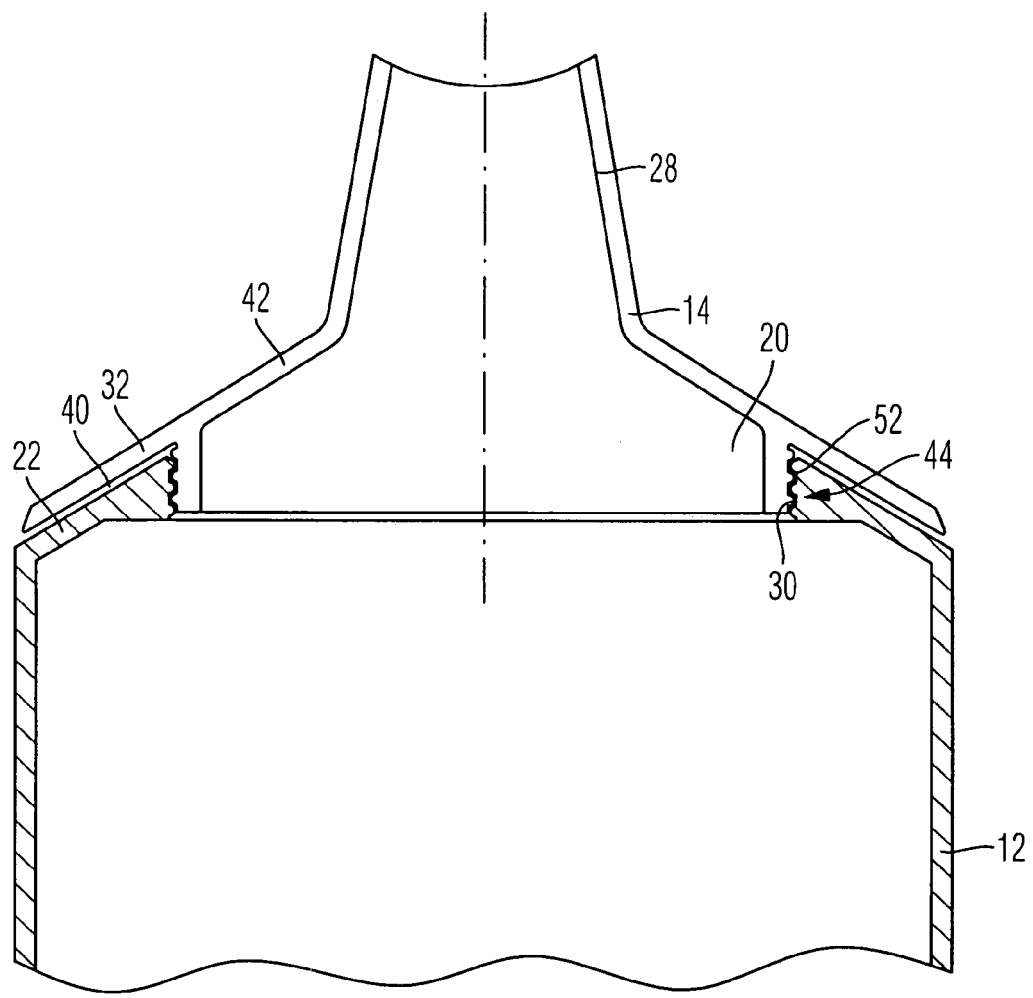
FIG. 3 is a further embodiment of the application device according to the invention, partially in schematic representation.

The mounting flange 30 is provided with positive or form-fit elements at its outer edge 44, for example a thread as shown in FIG. 3, which is designed for engagement with a respective positive or form-fit element at the opening of the outlet port 20 of the cartridge 12. In order to form this outer edge 44 that substantially extends parallel to the axis 34, the conical body 42 comprises a groove 46 that is provided along the entire periphery, and through which the vent duct 40 extends, as can be seen in FIG. 2a in the right-hand area. From FIG. 2a it is further obvious that the vent duct 40 does not extend straight ahead but is bent 90° twice in the area of the groove 46. In the further course of the vent duct 40, some kind of saw tooth profile or thread design 50 is provided between the conical edge 22 and the covering collar 32, the saw tooth profile in the exemplary case being provided at the inside of the covering collar 32.

FIG. 3 shows in which manner the vent duct 40 can extend in the transition region between the cartridge 12 and the application nozzle 14. At this location a thread 52 is provided by means of an engagement of an internal thread (not shown in detail) of the outlet port 20 and an external thread at the outer edge 44 of the mounting flange 30. Said thread is formed so that deliberately at least partially some clearance or play is left or the vent duct extends through the thread. This can be implemented or realized with the aid of interruptions of the thread pitch, different thicknesses and alternating through holes or for example also with the aid of some corrugation of one of the thread pitches in order to improve the permeability for air, although the thread guide relative to one another is not degraded.

FIG. 3 shows that the vent duct 40 is formed along the entire periphery. It shall be understood that instead of the circumferential embodiment, the vent duct can also only be provided on one side, for example, if the position of the cartridge 12 is fixed in an application device, more precisely if it has definitely been confirmed which position forms the highest point of the cartridge during operation.

Figure 4:
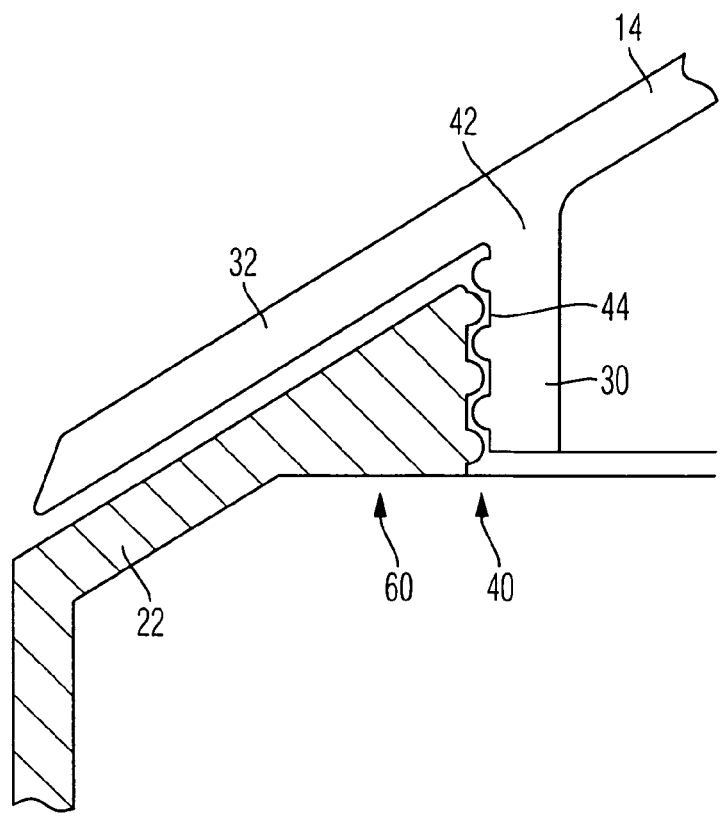
FIG. 4 is a further representation of a detail of an application device according to the invention in a further embodiment.

FIG. 4 is an enlarged representation and shows in which manner air can escape through the vent duct 40, whereas like or corresponding elements have the same reference numerals as it is the case with the further figures. As can be seen from FIG. 4, the vent duct 40 extends along a seal or gasket 34 between the application nozzle 14 and the conical edge 22 of the cartridge. The seal or gasket extends at least partially along a perimeter region of the outlet port. Optionally, one or several elastic lips 48 can be arranged one after another in the direction of flow within the vent duct 40.

Figure 5:
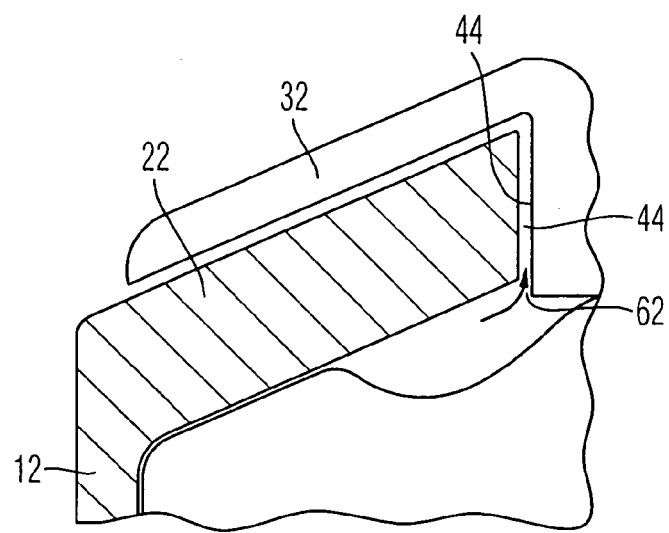
FIG. 5 is a further detail representation of a further embodiment of an application device according to the invention.

FIG. 5 shows a further modified embodiment of a cartridge 12 that at its inside is devoid of straight surfaces according to the surface 60 in FIG. 4. This solution, for example, is well suitable for an upright position of the cartridge 12 since the highest point of the cartridge is then formed at the inlet slot 62 of the vent duct 40.

Here in this embodiment, the vent duct 40 is formed straight and unobstructed with only one deflection, whereas it is to be understood that the shape of the vent duct to a large extent can be adapted to the requirements. The vent duct of FIG. 5 may be provided with a filter 38.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the terms as used in the claims are intended to include not only the designs illustrated in the drawings of this application and the equivalent designs discussed in the text, but are also intended to cover other equivalents now known to those skilled in the art, or those equivalents which may become known to those skilled in the art in the future.

What is claimed is:

1. Application device for dental materials comprising a cartridge having a piston and being adapted to receive the dental material, said application device further comprising an application nozzle that covers an outlet port of the cartridge and that is positively connected with the cartridge, and a transition region whereat the cartridge interfaces the application nozzle, wherein the application nozzle (14) and/or the cartridge (12) or the transition region thereof at least comprise one vent duct (40) that extends outwardly from the interior of the cartridge and whose inner width or diameter blocks the discharge of dental material and wherein the vent duct is formed solely between the cartridge and the application nozzle.

2. Application device as claimed in claim 1, wherein a section of the cartridge (12) proximate the outlet port (20) has the shape of a tapered truncated cone and wherein a connecting region of the application nozzle (14) comprises a corresponding counter contour and wherein a taper of the connecting region of the application nozzle (14) is at least partially covered.

3. Application device as claimed in claim 1, wherein the vent duct (40) extends along a seal or gasket between the application nozzle (14) and the cartridge (12) between ends of the seal or gasket, said seal or gasket at least partially extending along a perimeter region of the outlet port (20).

4. Application device as claimed in claim 1, wherein at least part of the vent duct (40) comprises at least one deflection at the seal or gasket, thus elongating the vent duct, said vent duct (40) having the shape of a labyrinth.

5. Application device as claimed in claim 1, wherein the dental material collects or accumulates at the inlet of the vent duct (40) and seals the vent duct (40).

6. Application device as claimed in claim 1, wherein the vent duct (40) at least comprises a slot or narrow gap whose height is dimensioned so small that upon actuation of the piston dental material cannot penetrate or get through.

7. Application device as claimed in claim 6, wherein the gap is smaller than 1 mm, and wherein in the vent duct is a filter (38) that is permeable to air, is arranged.

8. Application device as claimed in claim 1, wherein the dental mass or material is a plastic material that can be cured by light and/or heat, and wherein the dental mass or material is especially used for the production of implants.

9. Application device as claimed in claim 1, wherein several elastic lips are arranged one after another in the direction of flow within the vent duct (40).

10. Application device as claimed in claim 2, wherein a section of the cartridge (12) has a circle-symmetric shape proximate the outlet port and/or the tapered truncated cone.

11. Application device as claimed in claim 2, wherein the vent duct (40) is arranged along the entire periphery, in the transition region between the tapered truncated cone and the application nozzle (14) and forms a barrier for the dental material.

12. Application device as claimed in claim 7, wherein the gap is smaller than 0.5 mm.

13. Application device as claimed in claim 1, wherein the dental mass or material is used for the production of dentures.

* * * * *